United States Patent

Pavia et al.

[11] Patent Number: 6,080,587
[45] Date of Patent: Jun. 27, 2000

[54] METHOD FOR PREPARING AND SELECTING PHARMACEUTICALLY USEFUL SULFUR-BRIDGED BI- AND TRIAROMATIC RING COMPOUNDS FROM A STRUCTURALLY DIVERSE UNIVERSAL LIBRARY

[75] Inventors: Michael Raymond Pavia, Newton; Harold Vernon Meyers, Belmont, both of Mass.

[73] Assignee: Eli Lilly and Company, Indianapolis, Ind.

[21] Appl. No.: 09/013,362

[22] Filed: Jan. 23, 1998

[51] Int. Cl.[7] .................. G01N 33/566; G01N 33/53; C12Q 1/00; C07C 317/00; C07C 319/00
[52] U.S. Cl. .................. 436/501; 436/518; 435/4; 435/7.1; 435/DIG. 34; 568/27; 568/28; 568/38; 568/39; 568/44; 568/45; 568/46; 568/49; 568/52; 568/53
[58] Field of Search .................. 436/501, 518; 568/27, 28, 38, 39, 44, 45, 46, 49, 52, 53; 435/DIG. 34, 4, 7.1

[56] References Cited

FOREIGN PATENT DOCUMENTS

95/04277  2/1995  WIPO .

*Primary Examiner*—Bennett Celsa
*Assistant Examiner*—Joseph W. Ricigliano
*Attorney, Agent, or Firm*—Charles T. Joyner; Daniel W. Collins

[57] ABSTRACT

Methods for rapidly generating large rationally designed libraries of structurally-diverse small molecular weight compounds using a multicombinatorial approach. Also disclosed are compounds of the formula

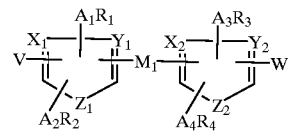

1 Claim, No Drawings

METHOD FOR PREPARING AND SELECTING PHARMACEUTICALLY USEFUL SULFUR-BRIDGED BI- AND TRIAROMATIC RING COMPOUNDS FROM A STRUCTURALLY DIVERSE UNIVERSAL LIBRARY

TECHNICAL FIELD

The invention relates to a method for preparing and selecting sulfur-bridged bi- and triaromatic ring compounds having desired pharmaceutical or other biological utility. More particularly, the invention is a method for preparing a structurally diverse library of low molecular weight compounds and then selecting from the library those compounds having the desired pharmacologic activity.

BACKGROUND INFORMATION

A key step in preparing and selecting pharmaceutically or other biologically useful compounds is identification of structurally-unique lead compounds. In 1990 it was estimated that nearly one-third of the $231 Million average cost for making a new therapeutic compound available for widespread public use was spent in identifying and optimizing a lead chemical structure. Traditionally and currently mass screening of large numbers of compounds and mixtures of compounds has been and is the most successful method for identifying chemical leads. Recent availability of robotic, rapid, high throughput biological screens is beginning to make possible efficient screening of hundreds of thousands of compounds per year.

Most screening libraries consist of a historical collection of compounds synthesized in the course of pharmaceutical research, natural products, and, more recently, peptide libraries. Each of these libraries has limitations. Historical pharmaceutical collections of synthesized compounds contain a limited number of diverse structures which represent only a small fraction of total structural diversity possibilities. Limitations of natural products libraries include the structural complexity of the leads identified and the difficulty of reducing these leads to useful pharmaceutical agents. Peptide libraries are limited to peptides or peptide mimics; to date conversion of peptide chemical leads into pharmaceutically useful, orally active, non-peptide drug candidates in the absence of a small molecule chemical lead has been met with limited success.

Some of the peptide and peptide mimic libraries referred to above were prepared using combinatorial chemistry. A challenge facing medicinal chemists is to translate the success using combinatorial chemistry to prepare peptide and peptide-like compounds into technology suitable for efficiently preparing large libraries of low molecular weight non-peptide compounds. Solid phase chemistry for preparing low molecular weight compounds is desirable to effect such a translation. The following references are examples of the types of solid phase chemistry methods that may be useful in low molecular weight compound combinatorial chemistry.

In 1974, F. Camps et al. (Annales De Quimica 70, 848) reported solid phase synthesis of four related benzodiazepines. More recently Bunin and Ellman (J. Am. Chem. Soc. (1992) 114, 10997, and Proc. Nat. Acad. Sci. USA (1994) 91, 4708) and S. H. DeWitt et al., (Proc. Nat. Acad. Sci. USA (1993) 90, 6909) also reported preparation of a small number of benzodiazepines using solid phase chemistry. Two tetradecene-1-ol acetates also have been prepared on solid supports (C. C. Leznoff et al., Can. J. Chem. (1977) 55, 1143). Additionally, solid phase synthesis of 4,4'-stilbenecarbaldehyde has been reported (J. Y. Wong et al., Angew. Chem. Int. Ed. (1974) 13, 666).

The following references are examples of biphenyl and triphenyl compounds that have been prepared by well known synthetic organic chemical methods. A. A. Patchett et al. recently reported that certain biphenyl acylsulfonamides and biphenyl sulfonylcarbamates are orally active antagonists of the angiotensin II receptor (Medicinal Chemistry Abstract #80 (1993) ACS Meeting-Chicago). Other recently reported angiotensin II antagonists include several imidazopyridine and tetrazole-substituted biphenyl compounds (E. M. Naylor et al., Medicinal Chemistry Abstract #76 (1993) ACS Meeting-Chicago) and a series of carbon-tethered biphenyl pyrrole compounds (J. M. Hamby et al., Medicinal Chemistry Abstract #72 (1993) ACS Meeting-Chicago). Others recently have reported that certain ortho-biphenylphenols are leukotriene antagonists (M. J. Sofia et al., Medicinal Chemistry Abstract #5 (1993) ACS Meeting-Chicago).

Preparation of various other substituted biphenyls has been reported. An example of the many references describing methoxy substituted biphenyls is M. G. Banwell et al. which describes certain trimethoxy and tetramethoxy biphenyls that have tubulin binding properties (CA118(19):191308u (1992)). Another such reference describes synthesis of several methoxy and ethoxy-substituted biphenyls for use in a peroxidase indicator system for basic media (CA118(1):3411a (1992)). 2,4',5-Trimethoxy-4-biphenylcarboxylic acid has been reported to have estrogenic activity (CA54:19584c (1959)).

Synthesis of 2,2',5,5'-(tetrapropynl-1-oxy)biphenyl has been reported without indication of its use (CA116(11):105745p (1991)). Similarly, 2,2',6,6'-tetrabenzyloxybiphenyl has been reported (CA110(21):192346b (1988)) and 2,2',3,3'-tetramethoxymethylbiphenyl (CA97(11):91847y (1982)) have been reported without a suggested utility. Preparation of several trisubstituted and tetrasubstituted biphenyls and terphenyls has been reported (CA118(21):212566u (1993)).

Preparation of substituted bisphenyl compounds having a bridging group between the two phenyl rings has been reported. K. Edogawa et al. disclosed substituted bisphenyl compounds having $SO_2$, S, $CMe_2$, or O moieties between the rings that are useful in making semipermeable composite membranes for liquid separation (CA109(18):151003y (1986)). Several tetrahydroxy substituted bisphenyl methanes without an indication of their utility have been reported (Marsh et al. Ind. Eng. Chem. (1949) 41, 2176).

Thus there remains a need for methods to efficiently prepare large libraries of low molecular weight non-peptide compounds and to select from such libraries compounds having desired pharmaceutical utility.

SUMMARY OF THE INVENTION

The presently invented method for preparing and selecting sulfur-bridged bi- and triaromatic ring compounds having desired pharmaceutical or other biological utility includes a system for rapidly generating large rationally designed libraries of structurally diverse small molecule compounds to explore multiparameter space that overcomes many of the disadvantages associated with using currently available libraries as a basis for identifying and selecting new pharmaceutical agents. The disclosed invention makes possible preparation of libraries of low molecular weight organic chemical compounds which have diverse chemical structures that are known and can be controlled. Additionally, other characteristics of the compounds that are important for pharmaceutical utility, such as solubility, can be controlled. Most importantly, however, because the compounds prepared using this invention are low molecular weight non-peptide compounds they are expected to be useful in a much broader spectrum of therapeutic applications than peptides which generally can only be administered by injection or inhalation.

DETAILED DESCRIPTION OF THE INVENTION

The presently invented method for preparing and selecting sulfur-bridged bi- and triaromatic ring compounds having desired pharmaceutical or other biologic utility includes a multiple combinatorial approach to prepare structurally diverse libraries which contain biologically useful compounds. Combinatorial chemistry takes advantage of the nature of the interaction between biological ligates such as antibodies, receptors, enzymes, ion channels, and transcription factors, and their ligands such as antigens, hormones, neurotransmitters, and pharmaceutical agents. It generally is agreed that ligate/ligand affinity and interaction results from binding or interaction between at least three functional groups or chemical functionalities on the ligand and complementary sites on the ligate. Strong interactions between ligates and ligands are dependent upon the properties and three dimensional spacial orientation of the functional groups or chemical functionalities on the ligands. High affinity specific ligands for a given ligate have functional groups that: (1) bind tightly to the binding sites on the ligate and (2) are positioned to bring the functional groups into close proximity with the ligate binding sites in the biological milieu where the interactions occur.

Compounds prepared using the invented method have molecular weights of between about 200 and 1000 daltons, preferably between about 300 and 600 daltons, and contain two component parts: (1) scaffold moieties and (2) at least three functional groups. As used herein a "scaffold" is a molecule onto which functional groups can be attached in a manner that when two or more scaffold moieties are attached results in the desired spacial orientation of the functional groups. Scaffold moieties preferably are selected such that they can be prepared from available materials by known chemical reactions and readily allow for attachment of desired functional groups and/or other scaffold moieties in a variety of positions on the molecule. In this specification and claims, as indicated by the context, "scaffold" may also refer to two or more attached scaffold moieties.

Suitable scaffolds are compounds of the following formula:

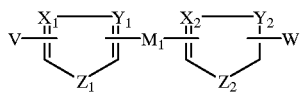

wherein:

$M_1$ and $M_2$ independently are S, SO, $SO_2$, $SO_2NR'$, or $NR'SO_2$ wherein R' is H or $C_{1-6}$alkyl;

$X_1$, $Y_1$ and $Z_1$ are any accessible combination of CH, CHCH, O, S, N, and NH provided that at least one is CH or CHCH and not more than one is CHCH;

$X_2$, $Y_2$ and $Z_2$ are any accessible combination of CH, CHCH, O, S, N, and NH provided that at least one is CH or CHCH and not more than one is CHCH;

V is H, $C_{1-6}$alkyl, halo, $(C_{0-4}alkyl)OH$, $(C_{0-4}alkyl)SH$, $(C_{0-4}alkyl)NR_{22}R_{23}$, or $(C_{0-4}alkyl)CO_2R_{76}$;

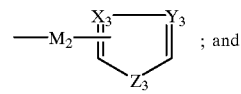; and $X_3$, $Y_3$, and $Z_3$ are any accessible combination of CH, CHCH, O, S, N, and NH provided that at least one is CH or CHCH and not more than one is CHCH.

Preferred scaffolds are: (1) bisphenyl, (2) trisphenyl, (3) bispyridyl, and (4) pyridyl-phenyl wherein the bridging group between the rings is as defined for $M_1$ and $M_2$ above.

Useful functional groups include the side chains of the 19 naturally occurring L-amino acids and the side chains of nucleotides found in nature. Additionally, non-naturally occurring mimics of these groups are useful. Preferred compounds of the invention which are prepared by combining preferred scaffold moieties with preferred functional groups are shown in Formula I below:

Formula I

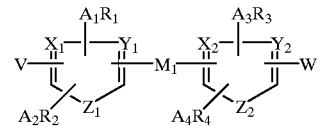

wherein:

$X_1$, $Y_1$ and $Z_1$ are any accessible combination of CH, CHCH, O, S, N, and NH provided that at least one is CH or CHCH and not more than one is CHCH;

$X_2$, $Y_2$ and $Z_2$ are any accessible combination of CH, CHCH, O, S, N, and NH provided that at least one is CH or CHCH and not more than one is CHCH;

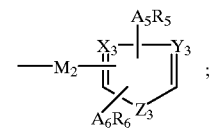;

$X_3$, $Y_3$ and $Z_3$ are any accessible combination of CH, CHCH, O, S, N, and NH provided that at least one is CH or CHCH and not more than one is CHCH;

$M_1$ and $M_2$ independently are S, SO, $SO_2$, $SO_2NR'$, or $NR'SO_2$ wherein R' is H or $C_{1-6}$alkyl;

V is H, $C_{1-6}$alkyl, halo, $(C_{0-4}alkyl)OH$, $(C_{0-4}alkyl)SH$, $(C_{0-4}alkyl)NR_{22}R_{23}$, or $(C_{0-4}alkyl)CO_2R_{76}$;

$A_1$, $A_2$, $A_3$, $A_4$, $A_5$, and $A_6$ independently are absent or present as O, S, $NR_{60}$; or $C_{0-6}alkylC(O)NR_{21}$, provided that at least three are present;

$R_1$, $R_2$, $R_3$, $R_4$, $R_5$ and $R_6$ independently are H, $(C_{0-6}alkyl)$ $COR_{15}$, $(C_{1-6}alkyl)R_{16}R_{17}$, $(C_{1-6}alkyl)OR_{24}$ except methoxymethyl, $(C_{1-6}alkyl)NR_{25}R_{26}$, $(C_{0-6}alkyl)$ $NR_{80}C(NR_{81})NR_{82}R_{83}$, $C_{1-6}$-alkyl-D, or $C_{1-6}$alkylindole;

D is one or multiple fused saturated or unsaturated five or six membered cyclic hydrocarbon or heterocyclic ring system containing one or two O, N, or S atoms that is unsubstituted or substituted by any accessible combination of 1 to 4 substituents selected from $C_{1-6}$alkyl, $NR_7R_8$, $OR_9$, $SR_{10}$, or $COR_{11}$, halogen, $CF_3$;

$R_7$, $R_8$, $R_9$, $R_{10}$, $R_{12}$, $R_{13}$, $R_{14}$, $R_{20}$, $R_{21}$, $R_{22}$, $R_{23}$, $R_{60}$, $R_{75}$, $R_{76}$, $R_{77}$, $R_{78}$, $R_{80}$, $R_{81}$, $R_{82}$, and $R_{83}$ independently are H or $C_{1-6}$alkyl;

$R_{16}$, $R_{17}$, $R_{18}$, $R_{19}$, $R_{24}$, $R_{25}$, and $R_{26}$ independently are H, $C_{1-6}$alkyl, phenyl, or substituted phenyl;

$R_{11}$ is $OR_{12}$ or $NR_{13}R_{14}$;

$R_{15}$ is $OR_{18}$ or $NR_{19}R_{20}$; or any pharmaceutically useful salt thereof.

The compounds of Formula I constitute a universal library of compounds that includes pharmaceutically useful compounds.

As used in Formula I and elsewhere in this specification and the claims, "$C_{x-y}$alkyl" is a straight chain or branched, saturated or unsaturated alkyl group containing x to y carbon atoms wherein x and y are integers and "halo" includes bromo, chloro, fluoro, and iodo, and "substituted phenyl" is a phenyl group substituted by any accessible combination of halo, $CF_3$, OH, $C_{1-6}$alkyl, $C_{1-6}$-alkoxy, COOH, $COOC_{1-6}$alkyl, NRR, SR, or CONR wherein R is H or $C_{1-6}$alkyl.

In more preferred compounds of the invention $X_1$ to $X_3$, $Y_1$ to $Y_3$, and $Z_1$ to $Z_3$ are selected so that one or more of the ring systems is pyrrole, furan, thiophene, pyridine, pyrazole, pyrimidine or isoxazole with phenyl being most preferred. Also in more preferred compounds of the invention D is one of the following ring systems substituted as described above: pyrrole, furan, imidazole, thiophene, pyridine, pyrazole, pyrimidine, pyridazine, or isoxazole with phenyl being most preferred.

More preferred compounds of the invention are shown in the following Formula II:

Formula II

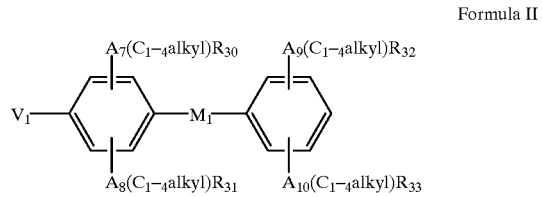

wherein:

$M_1$ is S, SO, $SO_2$, $SO_2NR'$, or $NR'SO_2$ wherein R' is H or $C_{1-6}$alkyl;

$V_1$ is H, $CH_3$, OH, or $CH_2OH$;

$A_7$, $A_8$, $A_9$, and $A_{10}$ independently are absent or present as O provided that at least three are O; and $R_{30}$, $R_{31}$, $R_{32}$, and $R_{33}$ independently are OH, $NH_2$, $CO_2H$, phenyl, substituted phenyl, $CONH_2$, $NR_{80}C(NR_{81})NR_{82}R_{83}$, $C_{1-6}$alkyl, imidazole, or indole wherein $R_{80}$ to $R_{83}$ are H or $C_{1-4}$alkyl.

Pharmaceutically useful salts of the above compounds include, for example, sodium, potassium, trialkyl ammonium, calcium, zinc, lithium, magnesium, aluminum, diethanolamine, ethylenediamine, megulmine, acetate, maleate, fumarate, lactate, oxalate, methansulfonate, ethanesulfonate, benzenesulfonate, tartrate, citrate, hydrochloride, hydrobromide, sulfate, phosphate, and nitrate. Other pharmaceutically useful salts are readily apparent to skilled medicinal chemists.

Some of the compounds included in Formula I can exist in more than one chiral form and thus exhibit stereoisomerism. Formula I includes all purified stereoisomers and racemic mixtures of the compounds within its scope.

In one aspect of the invention a preliminary step in preparing and selecting compounds having desired pharmaceutical or other biologic utility is preparation of a universal library. As stated above medicinal chemists and pharmacologists generally agree that interactions between biological ligates and ligands require that the ligand contain at least three functional groups in a spacial orientation that is complementary to the binding sites on the ligate. It also is known that the distance between the binding sites on ligates is determined by the conformation of the ligate as it exists in its native environment and that effective ligands are those that have functional groups positioned to be complementary to such conformation. Because ligates are three dimensional in their natural setting, for any selected intramolecular distance between binding sites an essentially infinite number of possible specific positions for the binding sites exist. Thus there similarly is a very large number of possible functional group positions on the ligands that effectively interact with particular ligates. As used in this specification and claims a universal library is a collection of related small molecular weight compounds that with respect to spacial orientation of functional groups effectively samples a large segment of the possible specific positions with a selected distance and a sub-universal library is a universal library that is targeted to a particular biological ligate.

Preparation of bradykinin antagonists provides an example of the general approach to designing a sub-universal library. Bradykinin is a naturally-occurring nonapeptide that is formed enzymatically in the blood and extracellular fluids after injury (a review covering all aspects of bradykinin has appeared (M. Hall, Pharmac. Ther. 56 (1992) 131).

At least two distinct receptor types, B1 and B2 appear to exist. Although activation of B2 receptors appears to underlie the most relevant biological actions of kinins, both B1 and B2 receptors could be important in developing therapeutic strategies. Bradykinin is a major pain producing substance that excites and sensitizes sensory nerves following trauma, burns, injury and infection. Peptide bradykinin antagonists block bradykin-ininduced pain in animal models suggesting that a bradykinin antagonist would be effective for the treatment of a variety of painful disorders. Bradykinin has also been found in plasma exudates taken from the scalp of migraneurs and has been shown to cause severe vascular head pain upon intravenous injection suggesting that bradykinin antagonists would be useful for the treatment of headache. Bradykinin is a potent vasodilator of most peripheral arteries and also causes neurogenic inflammation by the peripheral release of substance P, neurokinin A, and CGRP from sensory nerve fibers. Bradykinin has also been found in fluid from arthritic joints. These results suggest that bradykinin antagonists might have an important role as antiinflammatory agents. Bradykinin has been proposed to play a role in the pathogenesis of asthma as well.

While an orally-active bradykinin antagonist is likely to be of immense therapeutic benefit, the potent bradykinin agonists and antagonists reported to date have been peptide derivatives similar in size to bradykinin (which like bradykinin are expected to be rapidly degraded in body fluids).

Peptide analogs of bradykinin have shown that in general, replacement of Pro 7 with D-Phe or conformationally-constrained analogues as well as replacement of Phe 5 and 8 with thienylalanine or conformationally-constrained phenyl analogues affords competitive and selective antagonists of bradykinin. The C-terminal arginine is crucial for receptor activity. It appears that the N-terminal amino group is not necessary for activity since it can be acylated or removed without significant loss of activity. B1 selective antagonists are obtained by making the des-9 Arg analogues.

As an example, $D-Arg^0-Hyp^3-Thi^5-D-Tic^7-Oic^8$-bradykinin is a specific, potent, and long-lasting bradykinin antagonist being developed by Hoechst (Hoe-140) for allergic rhinitis and asthma. Furthermore, Kyle et al. have incorporated unnatural amino acids in the C-terminus of bradykinin which introduce B-turn stability and conclude that a B-turn in the four C-terminal amino acid residues might be a prerequisite for high receptor affinity (D. J. Kyle et al., J. Med. Chem. (1991) 34 (3): 1230–33).

Using the information described above it is possible to design a sub-universal library that is likely to possess bradykinin antagonist activity. The B-turn likely at the C-terminal portion of bradykinin suggests that the peptide antagonists are not fully extended at the receptor and likely occupy a distance of 10–18 Å. This is an ideal size to be mimicked by a bisphenyl scaffold and the size, shape, and group variations are explored by preparing a large library of compounds guided, or limited, by previously reported SAR studies on bradykinin receptor antagonists. This approach can be carried over to $B_1$ receptors by leaving out the arginine mimic on the A-ring. Using the previously described SAR data on bradykinin peptide antagonists the following compounds of Formula III are expected to include bradykinin antagonists:

Formula III wherein:
$M_1$ is S, SO, $SO_2$, $SO_2NR'$, or $NR'SO_2$ wherein R' is H or $C_{1-6}$alkyl;

B and B' are H, $O(CH_2)_n NR_{40}C(NR_{41})NR_{42}R_{61}$, or $O(CH_2)_n NR_{43}R_{44}$ wherein $R_{40}$, $R_{41}$, $R_{42}$, $R_{43}$, $R_{44}$, and $R_{61}$ independently are H or $C_{1-3}$alkyl, n and n' are 2 or 3; provided one of B and B' is H;

wherein X is CH, N, NH, O, or S; n is 1–3; n' is 1 when X is O, S, or NH; and n' is 2 when X is CH or N;

F, F', and F" are H, $O(CH_2)_n NR_{45}C(NR_{46})NR_{47}R_{62}$, or $O(CH_2)_n NR_{48}R_{49}$ wherein $R_{45}$, $R_{46}$, $R_{47}$, $R_{48}$, $R_{49}$, and $R_{62}$ independently are H or $C_{1-3}$alkyl, and n and n' are 2 or 3; provided two of F, F', and F" are H;

G and G' are H, $O(CH_2)_n OR_{50}$, or wherein X' is CH, N, NH, O, or S;
$R_{50}$ is H or $C_{1-3}$alkyl; and
$R_{51}$ is H, $C_{1-3}$ alkyl, halogen, $CF_3$, OH, $OC_{1-3}$alkyl, or NRR wherein R is H or $C_{1-4}$alkyl; n is 1–3; n' is 1 when X is O, S, or NH; and n' is 2 when X is CH or N; provided one of G and G' is H.

In preferred compounds:

B or B' is $OCH_2CH_2NHC(NH)NH_2$;
E is

F and F'" are $OCH_2CH_2NHC(NH)NH_2$;
G and G' are H; and
$M_1$ is S, SO, $SO_2$, $SO_2NR'$, or $NR'SO_2$ wherein R' is H or $C_{1-6}$alkyl.

These compounds are tested for bradykinin antagonist activity using a high-volume biochemical binding assay such as is referenced in the examples below. For potential use in rapid mass screening, a rat B2 receptor has been cloned by Jarnagin et al. (PNAS (1991) 88, 7724). It appears to be a 7-transmembrane domain G-protein coupled receptor with a molecular weight of 42 kD and 366 amino acids. Furthermore, a human B2 receptor was cloned by Hess et al. (Biochem. Biophys. Res. Comm. (1992) 184, 260) and has a molecular weight of 41.1 kD and 364 amino acids with 81% sequence homology to the rat B2 receptor. The binding assays are followed by examination of the compound in an in vitro smooth muscle preparation. Functional activity is assessed by examining in vitro PI turnover. In vivo models include bradykinin paw pressure in rats, both IP and PO.

Most of the remaining seven transmembrane G-protein coupled receptors (GPCR) are viable candidates for the approach described herein. Such receptors include, but are not limited to, CCK, angiotensin, bombesin, bradykinin, endothelin, neuropeptide Y, neurotensin, opiod, somatostatin, tachykinin (NK-1, NK-2, NK-3), thromboxane $A_2$, and vasopressin. The angiotensin-2 receptor might be of particular interest as a test case in light of the recently reported activity of a number of functionalized bisphenyl molecules.

The ligands for many of the GPCRs range from small-medium sized organics to small-medium peptides (4–35 amino acids). Most of these ligands are expected to occupy a 10–30 cubic Å volume making them ideal candidates for the libraries described herein. An increasing number of modeling and mutagenesis studies are not only indicating the appropriate approximate size but are also giving specific information on important residues of the receptor that interact with the ligand. This information can be readily applied to the design of receptor specific sub-universal libraries.

Some examples of recently available information includes the $TXA_2$ receptor (Yamamoto et al., J. Med. Chem. (1993) 36, 820–25). These workers propose the $TXA_2$ binding site and suggest specific residues of the receptor that are important for ligand binding, including Ser-201, Arg-295, and Trp-258. Groups that are complimentary to these residues would be built into the sub-universal library.

The NK 1–3 receptors have been cloned and expressed and mutational studies are ongoing which suggest the binding site for NK-1 antagonists is likely to be around the junction of extracellular loop 2 and the top of TMV and TMVI. Furthermore, the identification of non-peptide leads for the NK-1 receptor suggests some groups that allow initial selection of groups for a sub-universal library (Watling, TIPS (1993) 14, 81). It is believed that NK-1 antagonists will be useful for treating pain, inflammation, arthritis, and asthma.

Identification of residues for design of a somatostatin sub-universal library is guided by the work of Hirschmann et al. (J. Amer. Chem. Soc. (1992) 114, 9217).

Preparation of compounds that interact with ion channels provides another example of designing a sub-universal library. Ion channels are proteins which span cell membranes providing pathways for the flow of ions such as chloride or potassium. These channel proteins are involved in many cellular functions such as nerve signaling, muscle contraction and hormone secretion. Over the past several years there has been an explosive growth in the number of cloned and expressed ion channels, as well as in discoveries which link channels to disease. Moreover, now that it is clear that there are many subtypes of ion channels, differentially distributed throughout the body, the possibilities for selective targeting of specific channels in specific tissues are unlimited. This selective targeting will reduce unwanted drug-related side effects and toxicities.

Potassium channels can be divided into at least 6 major classes, and 15 subclasses, each with its own distinct biophysical and pharmacological identity. Agents which modulate specific potassium channels in specific tissues are expected to target select disease states without altering normal functions. Potassium channels are largely responsible for maintenance functions like establishing the membrane potential in unstimulated cells, or in switching on, or off, a cell's electrical activity. Thus, these channels in part control the cell's capacity for nervous transmission, muscle contraction and secretion. Due to their integral roles in almost all normal signal processing, agents which modulate potassium channels are likely to be useful for treating conditions such as diabetes and muscular sclerosis, cardiac arrhythmias and vascular hyperactivity.

Various types of ligand-activated and voltage-activated ion channels have now been cloned and functionally expressed. Sequence comparisons and hydropathy analyses have revealed a great deal of structural homology among these channels. Each channel sequence is composed of a repeating motif of transmembrane spanning domains which combine in various ways to form channels (For a recent review of the field, see Andersen and Koeppe, II, Physiological Reviews (1992) Vol. 72).

Site-directed mutagenesis has allowed researchers to probe the primary structure of ion channel proteins for critical amino acid residues involved in the binding sites of drug molecules. These studies will allow for the development of agents targeted for specific channel subtypes and binding sites. To date, several classes of ion channels, including potassium and chloride, have received intensive characterization leading to a basis on which to consider structure-based drug design.

Toxins, such as those from scorpion venoms, have proven useful in defining potential drug interaction sites on ion channels as well as defining physiological roles for channels. These peptide toxins which are 36–38 residues long, contain three disulfide bridges, and share strong sequence similarity among isoforms, block both voltage-gated and Ca-activated K channels with nanomolar affinity. Within this group of toxins, there are specific subtypes which bind to specific subtypes of potassium channels. Electrostatic interactions between charybdotoxin (CTX), a specific peptide pore blocker of K channels and a Ca-activated K channel have been extensively investigated. Charybdotoxin has eight positively charged residues (four lysines, three arginines, and one histidine). Electrostatic forces are known to favor CTX binding to the negatively charged mouths of K channels. However, only replacement of Arg25, Lys27, or Lys34 with a Gln residue strongly decreased the affinity of the toxin for the channel. These three residues are located close to one another on one side of the CTX molecule and make direct contact with the channel mouth. On the opposite side are five charged residues whose neutralization show little effect. Therefore the positively charged groups on CTX promote toxin channel interaction in two ways; by weak electrostatic influences and by direct and intimate contact with the channel on one side of the toxin molecule. The solution structure of CTX has been recently determined (Bontems et al., Biochemistry (1992) 31, 7756) and it has been shown that Arg25 and Lys34 are located within 10 Å of Lys27 and each is crucial for high affinity binding of CTX. The receptor site in the channel's mouth must be wide (>22 Å) and flat to accommodate the CTX molecule. The wide mouth must narrow abruptly into an ion-selective pore in order to provide a selective K binding site with which Lys27 interacts (Miller and Park, Biochemistry (1992) 31, 749, and Neuron (1992) 9, 307). These studies reveal a molecular surface of CTX which makes direct contact with the extracellular mouth of the K channel and a single CTX molecule physically occludes the K conduction pathway by binding to a receptor located in the externally-facing mouth of the channel protein.

Using the information described above, a sub-universal library targeted to K channels which mimics the three important binding residues both electronically (three positive charges) and spatially (6–18 Å total separation) is designed. Such a library is expected to identify non-peptide CTX mimics with therapeutic potential. The compounds of Formula IV represent a sub-universal library targeted to potassium channels:

Formula IV wherein:

$M_1$ is S, SO, $SO_2$, $SO_2NR'$, or $NR'SO_2$ wherein R' is H or $C_{1-6}$alkyl;

J, J', and M independently are $O(CH_2)_nNR_{50}C(NR_{51})NR_{52}R_{65}$ or $O(CH_2)_{n'}NR_{53}R_{54}$ wherein $R_{50}$, $R_{51}$, $R_{52}$, $R_{53}$, $R_{54}$, and $R_{65}$ independently are H or $C_{1-3}$alkyl, and n and n' independently are 2–3;

Q and Q' are H or $O(C_{1-4}alkyl)T$ wherein T is $C_{1-6}$alkyl, $CO_2R_{55}$, $OR_{56}$, or wherein:

$X_7$ is CH, N, NH, S, or O;

n''' is 1 when $X_7$ is NH, S, O; and 2 when $X_7$ is N or CH;

U is H, $C_{1-6}$ alkyl, halogen, $CF_3$, or $OR_{57}$; and $R_{55}$, $R_{56}$, and $R_{57}$ independently are H or $C_{1-6}$alkyl; provided that at least Q or Q' is H.

The presently invented multiple combinatorial method for preparing and selecting small molecular weight compounds having pharmaceutical utility or other biologic utility is used to efficiently prepare universal libraries. As used herein a multiple combinatorial method is a method for preparing compounds that uses two or more scaffold molecules each carrying functional group(s) that have been attached in a combinatorial fashion. Generally, compounds comprising two scaffold moieties are used for ligates of about 12 to 20 Å and compounds having three scaffold moieties yield ligands for ligates of about 20 to 35 Å.

The power of the invented multiple combinatorial method is demonstrated by the numbers of compounds that can be prepared quickly and efficiently. For example, using two scaffold molecules each containing two of twenty possible functional groups arranged in four different orientations yields more than 1,000,000 compounds. Using the same parameters with a third scaffold molecule allows for preparation of a universal library containing more than 1,000,000,000 compounds. The compounds of Formula I are an example of a universal library of compounds that are prepared according to the invention.

In another aspect the invention is used to prepare large quantities of a desired target compound rather than small amounts of multiple compounds as is the case in preparing universal or sub-universal libraries. Preferably when preparing universal or sub-universal libraries multiple compounds are prepared by simultaneously conducting different chemical reactions in multiple reaction vessels. Preferably, reactions are conducted simultaneously in about 25 reaction vessels, more preferably in about 100 reaction vessels, and most preferably in standard 96 well plates. To prepare large quantities of a selected compound the same reaction is carried out simultaneously in different reaction vessels.

The compounds and libraries of the invention preferably are prepared according to Scheme I below. In Scheme I the preferred method of synthesizing the compounds on a solid support is depicted. The libraries and compounds of the invention, however, also can be prepared using solution phase chemistry.

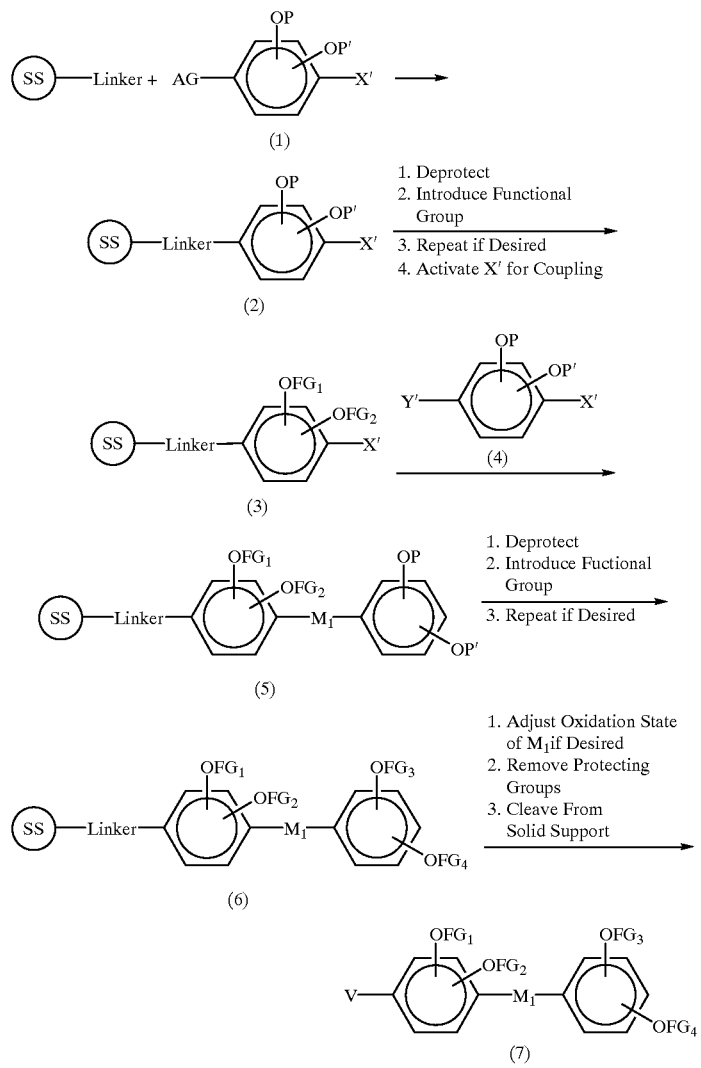

Scheme I demonstrates the invented method of preparing universal libraries of compounds. According to this scheme functional groups are attached to a first scaffold moiety to yield a compound comprising a scaffold and one or two functional groups (Compound 3). Thereafter a second scaffold molecule (Compound 4) is added with the formation of $M_1$ followed by addition of functional group(s) to the second scaffold moiety to yield Compound 6 which can have three or four functional groups. Compounds of Formula I then are prepared by adjusting the oxidation state of $M_1$ if needed followed by cleaving Compound 6 from the solid support.

In Scheme I "SS" is a solid support material such as the cross-linked polystyrene resin known as the Merrifield resin (R. S. Merrifield, J. Am. Chem. Soc. (1963) 85, 2149). Alternatively, any other suitable polymeric resin or other support material such as, for example, silica, glass, cotton, and cellulose is used. Also in Scheme I "AG" is any suitable group for attachment to the linker such as, for example, OH, $NH_2$, COOH, $CH_2OH$, $CH_2Br$, CHO, $CH_2Cl$, $CH_2SH$, SH and V is the same as in Formula I.

The linker group shown in Scheme I is any group that holds the first scaffold (Compound 1) onto the solid support and is formed by reaction of AG with the solid support, is stable to the reaction conditions necessary to complete the synthesis, and is easily cleavable upon completion of the synthesis. An olefin group also is used as a linker. In such case, for example, AG in Compound 1 is CHO and it is attached to the solid support using a Wittig-like reaction. When an olefin group is used the final product is cleaved from the linker by treatment with ozone or other known methods. A sulfide or oxygen bond is another suitable linker. When a sulfide or oxygen bond is the desired linker AG in Compound 1 is $CH_2$ halogen, preferably $CH_2Br$, and the bond between the solid support and Compound 1 is formed by reaction between the AG on Compound 1 and an SH or OH group on the solid support. Upon completion of the synthesis a sulfide or oxygen bond linker is cleaved by, for example, treatment with hydrogenolysis or dissolving metal reductions.

When a benzyl ester group is the desired linker AG in Compound 1 is $CH_2OH$ and the bond between the solid support and Compound 1 is formed by reaction between the AG on Compound 1 and a $CO_2H$ group on the solid support. Upon completion of the synthesis the benzyl ester group is cleaved by, for example, hydrogenolysis conditions.

P and P' in Scheme I are protecting groups for aromatic hydroxy groups. P and P' can be the same or different to allow for selective deprotection. Choice of P and P' also is influenced by compatibility with the chemistry to be used in the remainder of the synthesis. Preferred protecting groups are $C(O)CH_3$ and Ph-CO wherein "Ph" is phenyl. Deprotection of a $C(O)CH_3$ is performed by treatment with an amine according to known procedures and deprotection of a Ph-CO group is accomplished by treatment with a nucleophile such as methoxide using known conditions and procedures.

In Scheme I X' and Y' are groups that allow for formation of $M_1$. A preferred method for joining the rings is through reaction of an amino group on Compound 1 wherein X' is $NH_2$, with a sulfonyl chloride on Compound 4 wherein Y' is $SO_2Cl$. Alternatively, a preferred method for joining the rings is through reaction of a halo group on Compound 1 wherein X' is Br with a thiol.

When compounds having more than two scaffold moieties are desired the procedure of Scheme I is modified by repeating the steps needed to add one or more additional scaffolds before cleaving from the solid support. Also, the general procedure shown in Scheme I is used when scaffolds other than phenyl rings are used. Thus, any of the compounds included in Formula I can be prepared using Scheme I modified as may be necessary to accommodate different scaffold moieties. Any such necessary modifications are apparent to those skilled in the organic chemical synthetic arts.

As used in Scheme I "FG" is a functional group which may be the same or different at different positions on the compounds. Suitable functional groups are the $R_1$ through $R_6$ groups as defined in Formula I above. Although Scheme I shows preparation of compounds having two scaffold moieties and four functional groups such compounds having three functional groups are prepared by using a scaffold having one functional group in place of Compound 1 or Compound 4. Also, Compounds 1 and 4 provide for attachment of functional groups through an oxygen. By suitable replacement of these compounds a sulfur atom or a nitrogen atom can be used in place of one or more of the oxygens. Procedures for introducing functional groups onto the scaffolds are included in the examples below.

Scheme II is a modification of the Scheme I procedure that is used to prepare compounds wherein the functional group is attached to the scaffold moiety using a $(CH_2)_n C(O)NR'$ and n' is 0 and R' is H or $C_{1-6}$alkyl. In Scheme II AG, X', Y', and FG have the same meanings as in Scheme I.

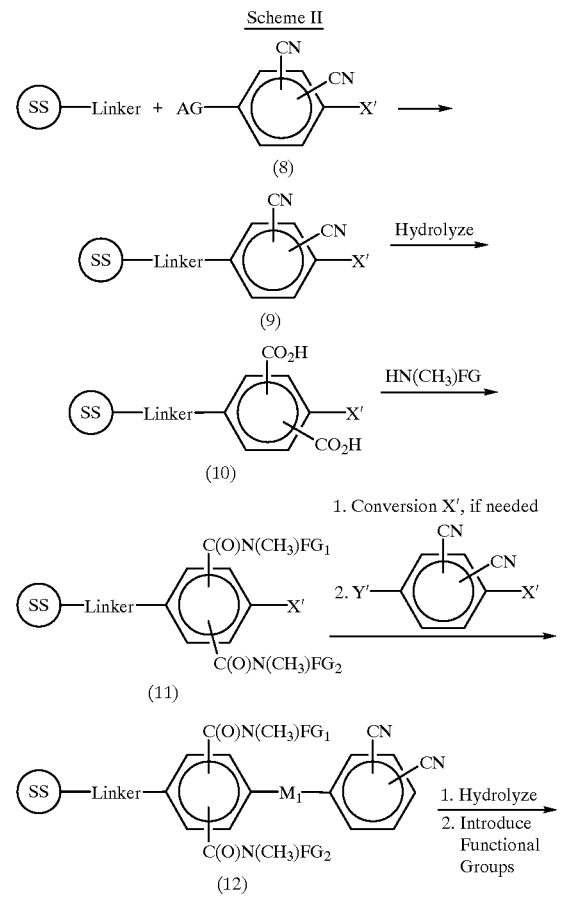

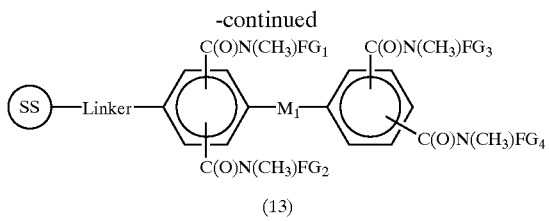

(13)

According to Scheme II a scaffold molecule having two cyano groups attached (Compound 8) first is attached to a solid support via a linker and then is hydrolyzed to yield free carboxylic acid groups (Compound 10). Then, functional groups are attached by treatment with HN(CH$_3$)FG to yield a scaffold with two functional groups (Compound 11). Next a second scaffold moiety with two cyano groups is attached to form M$_1$ as described in Scheme I followed by addition of functional groups to yield Compound 13. Compounds to be included in the libraries of the invention then are prepared by modifying M$_1$ if necessary, deprotecting and cleaving Compound 13 from the solid support as described in Scheme I.

Scheme III describes an alternate method of producing compounds wherein the functional groups are linked to the scaffold moieties via a C(O)N(CH$_3$) residue. In Scheme III X', Y', P, P', and FG have the same meanings as in Scheme I.

The disclosed invention includes the following Formula V compounds which are useful as intermediates in preparing the invented libraries and compounds:

Formula V

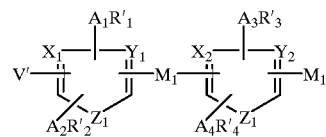

wherein:

W is H or

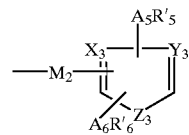

X$_3$, Y$_3$, Z$_3$, A$_5$, and A$_6$ are as defined in Formula I;

R'$_1$, R'$_2$, R'$_3$, R'$_4$, R'$_5$, R'$_6$ are a protecting group or R$_1$, R$_2$, R$_3$, R$_4$, R$_5$, and R$_6$ as defined in Formula I, provided that at least one of R'$_1$ to R'$_6$ is a protecting group;

V' is V as defined in Formula I or a bond to a solid support; and the remaining variables are as defined in Formula I.

As used in Formula V, a protecting group is any of the well known protecting groups that is suitable in view of the

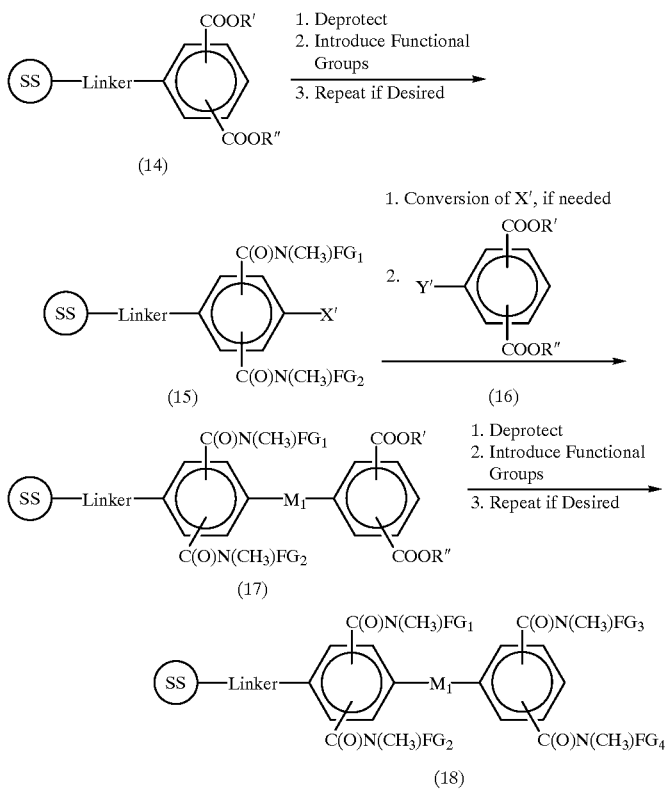

The starting compound in Scheme III (Compounds 14 and 16) are prepared by standard procedures. Compounds included in the invented libraries are prepared by cleaving Compound 18 from the solid support.

synthetic conditions used. Preferred protecting groups are C(O)CH$_3$ and Ph-CO.

Preparation of libraries of Formula I compounds is the first step in the invented method of preparing and selecting compounds having pharmaceutical or other biologic utility. After the libraries are prepared they are tested in a wide variety of in vitro and in vivo assays that are predictive of biologic activity and generally involve contacting the compounds with biological targets of interest and determining the strength of the interaction between the compounds and the biological target. Such assays are well known and include, without limitation, enzyme inhibition assays, such as protein kinase C and angiotensin converting enzyme, receptor binding assays, such as serotonin and excitatory amino acids, ion channel blocking, such as calcium, potassium and chloride, and transcription factor interaction. Generally, any activity identified in vitro is confirmed by evaluation in a suitable animal model if such is available and predictive of human pharmaceutical activity. The examples below include assays that are useful to select compounds of the invention that have pharmaceutical utility.

The compounds of Formula I that are useful as pharmaceutical agents can be incorporated into convenient dosage unit forms such as capsules, tablets, or injectable preparations. Pharmaceutical carriers which can be employed include, among others, syrup, peanut oil, olive oil, and water. Similarly, the carrier or diluent may include any time delay material, such as glyceryl monostearate or glyceryl distearate, alone or with a wax. The amount of solid carrier will vary widely but, preferably, will be from about 25 mg to about 1 g per dosage unit. If a liquid carrier is used, the preparation will be in the form of a syrup, emulsion, soft gelatin capsule, sterile injectable liquid such as an ampule, or an aqueous or non-aqueous suspension.

Pharmaceutical preparations are made following conventional techniques of a pharmaceutical chemist involving mixing, granulating, and compressing, when necessary, for tablet forms, or mixing, filling, and dissolving the ingredients, as appropriate, to give the desired oral or parenteral end products.

Doses of the pharmaceutically useful compounds of the invention will be an effective amount, that is, an amount necessary to produce the desired effect without producing untoward toxicity selected from the range of 0.1–1000 mg/kg of active compound, preferably 10–100 mg/kg. The selected dose is administered to a patient in need of treatment from 1–5 times per day, orally, rectally, by bolus injection, or by infusion.

EXAMPLES

The following examples illustrate but do not limit the scope of the invention disclosed in this specification.

Example 1

General Procedures

Scheme IV and the procedures that follow describe general procedures useful in preparing compounds of the invention.

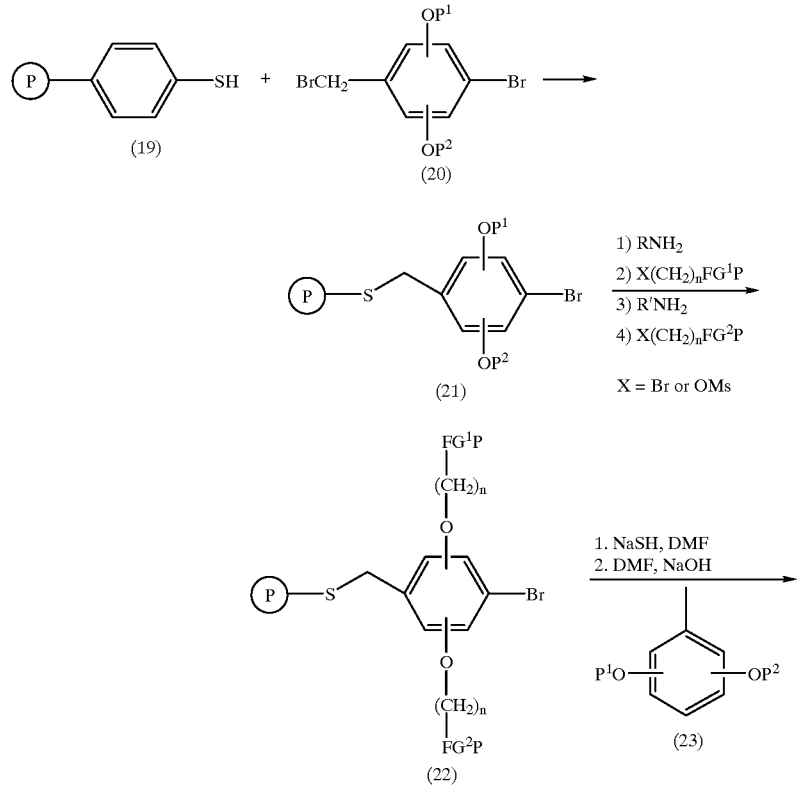

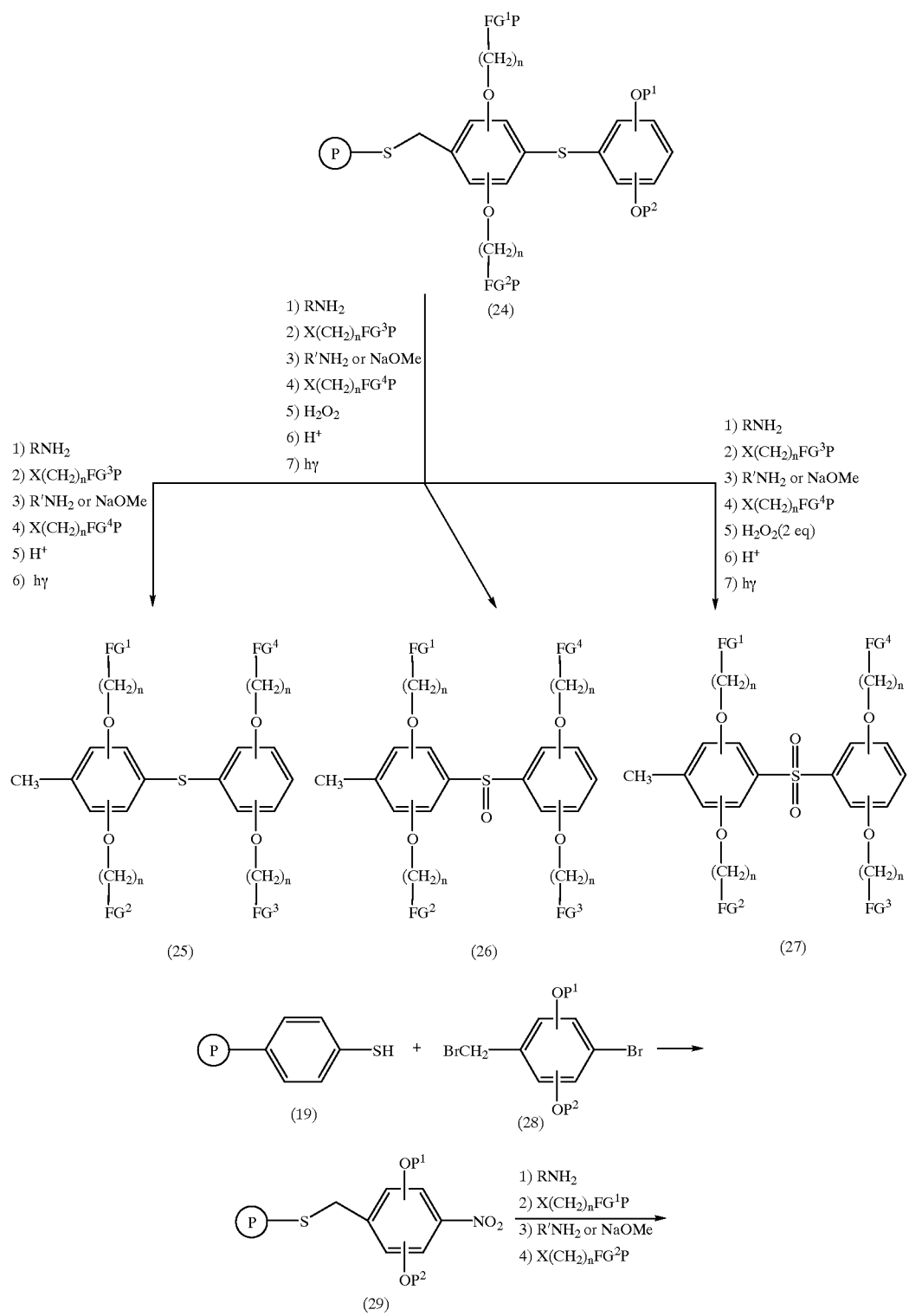

-continued
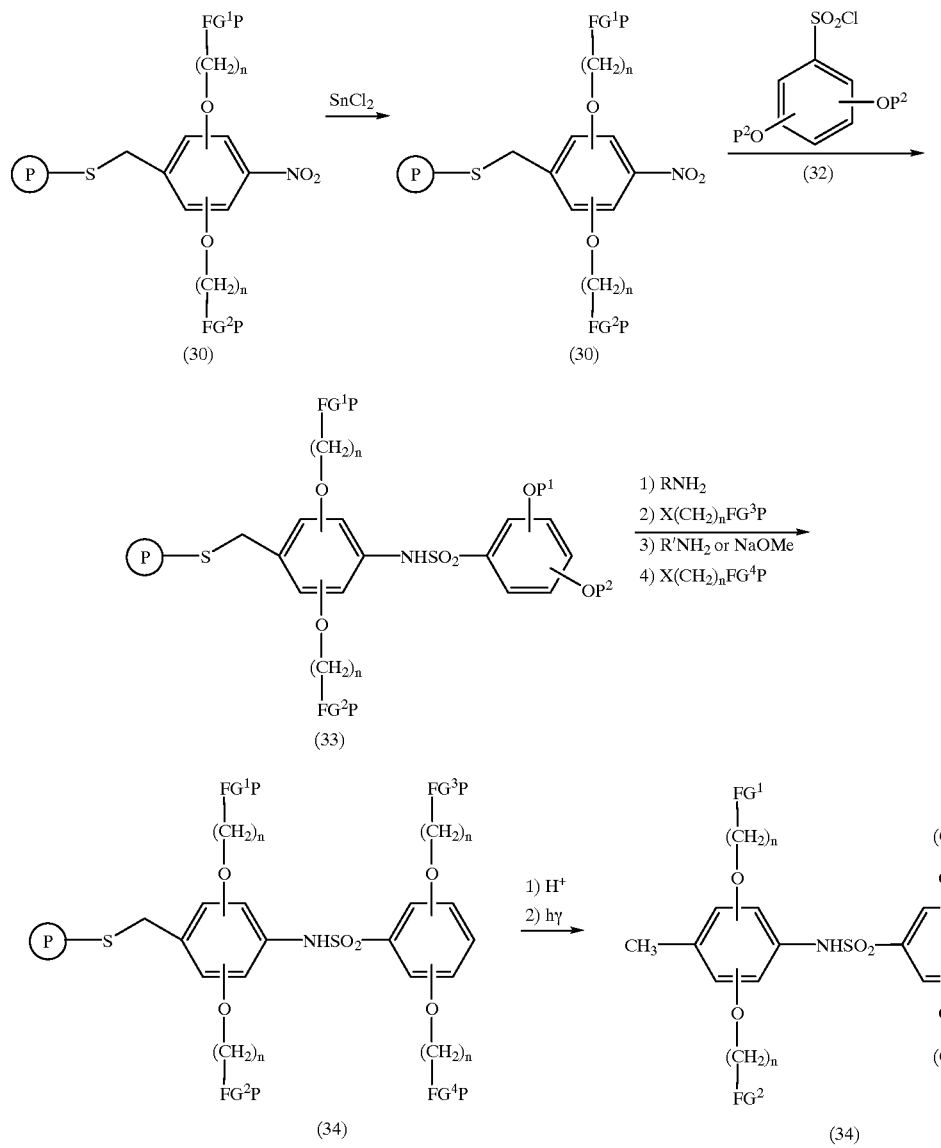
Scheme V
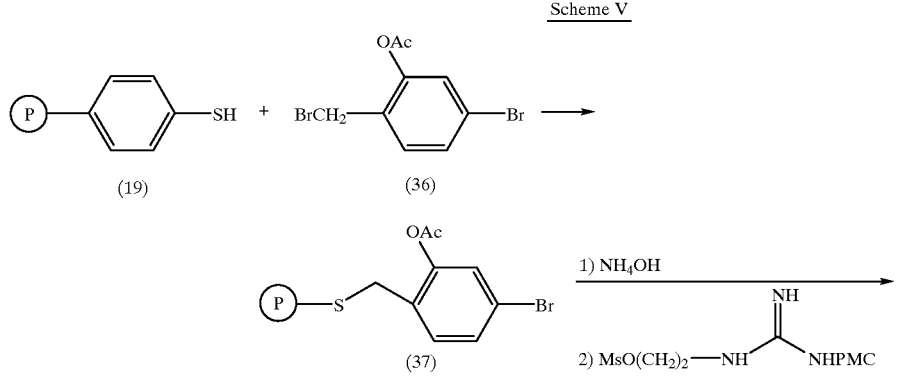

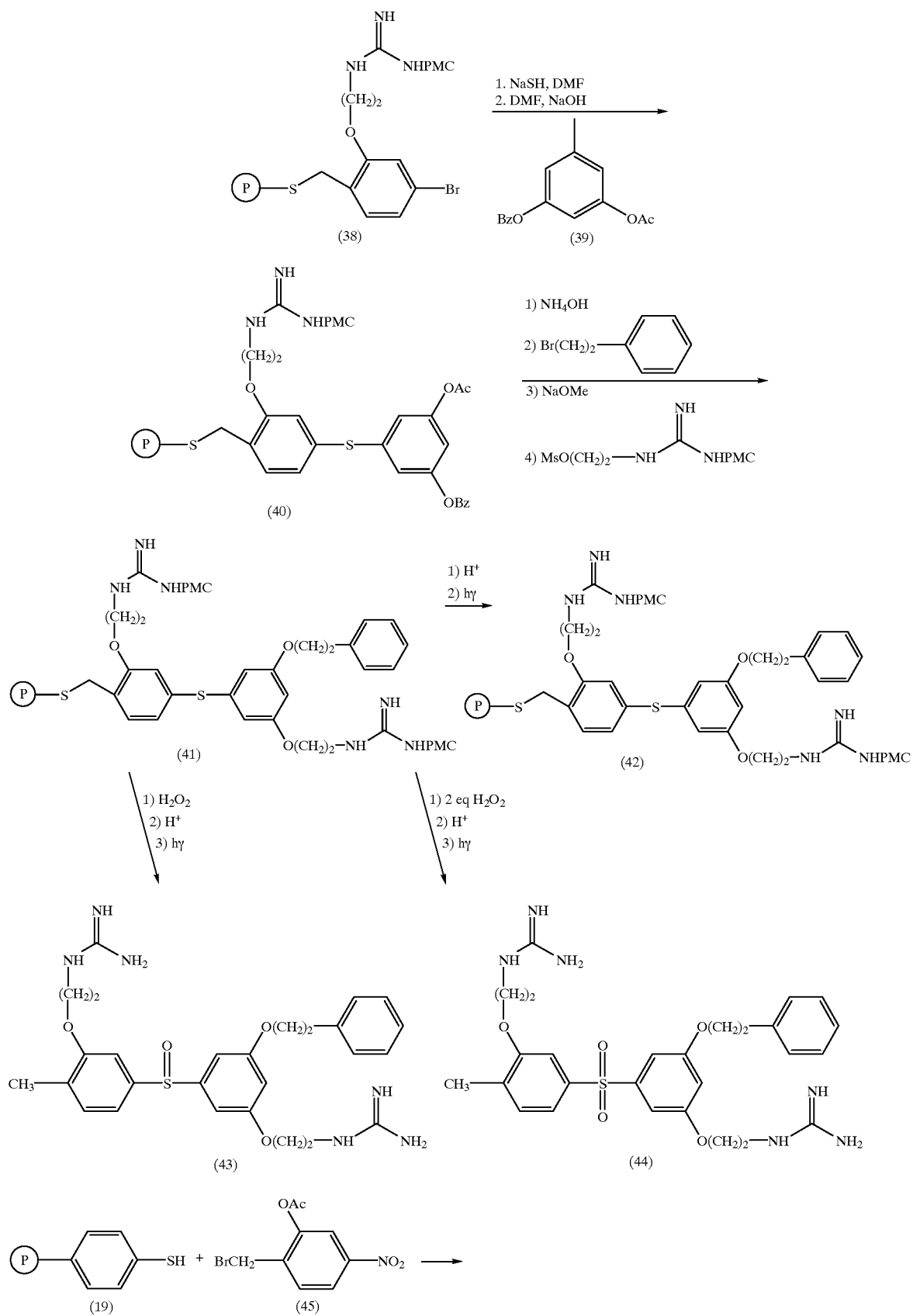

-continued
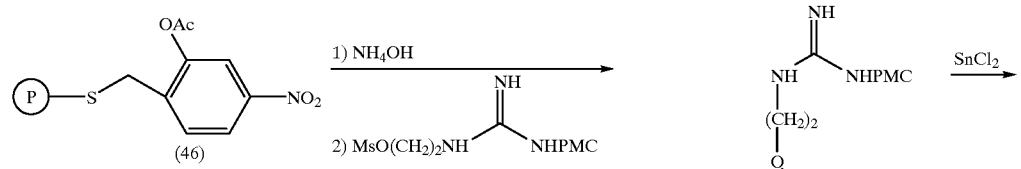
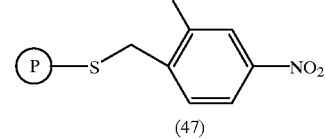
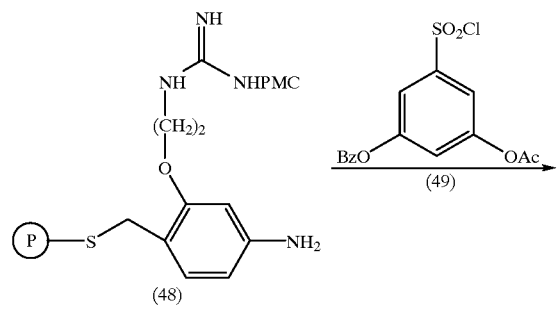
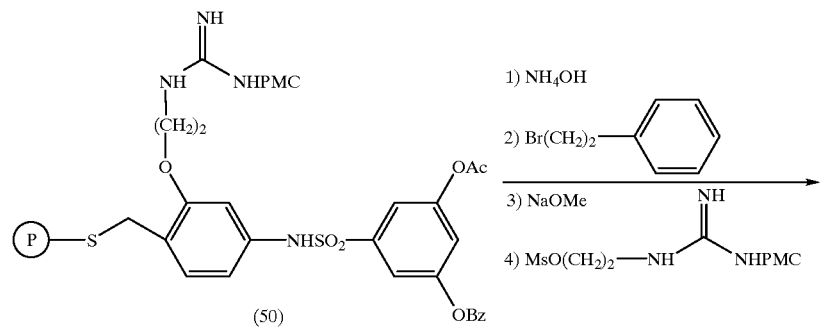
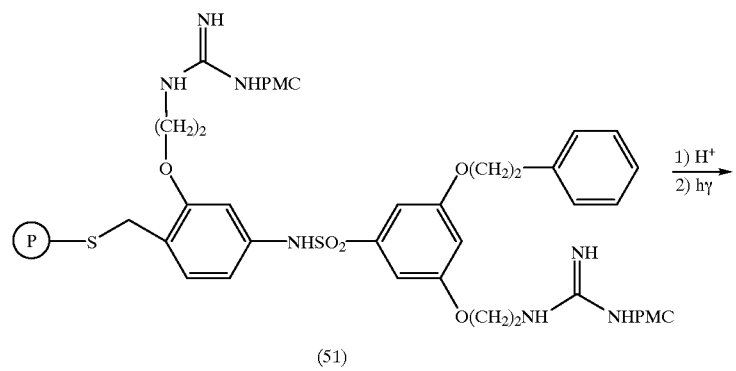
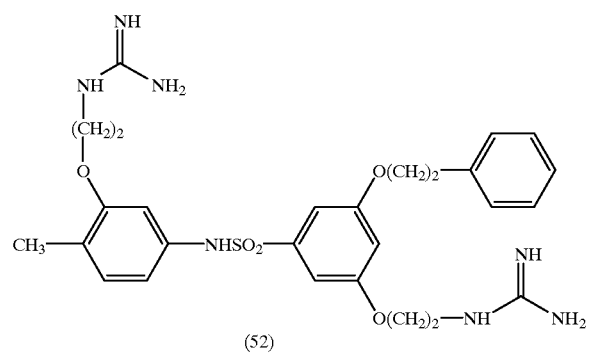

Example 1

General procedures for the preparation of tri- and tetra-substituted diphenylsulfides 25, diphenylsulfoxides 26, diphenylsulfones 27, and diphenylsulfonamides 35.

Preparation of resin 19: 2-Methoxy methyl phenylacetate was prepared by refluxing 2-methoxy phenylacetate (10.2 g, 61.3 mmole), 70 mL of anhydrous methanol and 1.5 mL of concentrated sulfuric acid for 17 hours. The solvent was removed and the oil was dissolved in 100 mL of diethyl ether, washed with saturated NaHCO$_3$, dried, filtered and evaporated to give 9.26 grams (83%) of 2-methoxymethyl phenylacetate. This material (10.0 g, 55.0 mmole) dissolved in 6 mL of tetrachloroethane was added over a period of 25 minutes (making sure that the temperature of the reaction mixture did not exceed 50° C.) to AlCl$_3$ (15 g, 112 mmole) in 50 mL of tetrachloroethane to which was added 2-bromopropionyl chloride (5.7 mL, 56.5 mmole) and the mixture heated at 45° C. for 20 minutes. The reaction was allowed to stir at 50° C. for 5 hours then at room temperature for 10 hours, poured onto 150 mL ice and 0.5 mL of concentrated HCl was added. The mixture was extracted with CH$_2$Cl$_2$ and the organic layer washed with 10% NaOH, and H$_2$O, dried, filtered and evaporated to give a dark purple-red oil which was purified by flash chromatography (SiO$_2$, first with 50% hexane-CH$_2$Cl$_2$ then with CH$_2$Cl$_2$) to afford 11.6 grams (66% yield) of methyl [3-(2-bromopropionyl)-6-methoxyphenyl]acetate as a thick oil: R$_f$=0.44 (SiO$_2$, CH$_2$Cl$_2$). This material (11.4 g, 36.3 mmole) was dissolved in 70 mL of acetone and 15 mL of concentrated HCl, 20 mL of H$_2$O were added and the resulting solution refluxed for 6 hours. The volatiles were removed to give an oil/water mixture which was then dissolved in 100 mL of CH$_2$Cl$_2$. The mixture was extracted with 150 mL of saturated NaHCO$_3$. The aqueous was then removed and acidified with concentrated HCl to a pH=1. The aqueous mixture was then quickly extracted with 100 mL of CH$_2$Cl$_2$. The organic layer was then dried, filtered, and evaporated to give 6.0 g (64%) of as a white solid: R$_f$=0.6 (SiO$_2$, 10% methanol-CH$_2$Cl$_2$). To the sodium salt of 2-methyl-2-propanethiol (0.9 g, 8.82 mmole) was added sodium hydride (0.25 g, 11.3 mmole) and 15 mL of anhydrous tetrahydrofuran and mixture cooled to 0° C. To the mixture was added the above 3-[(2-chloropropionyl)-6-methoxyphenyl]acetate (1.5 g, 5.84 mmole) dissolved in 15 mL of anhydrous THF over a period of 10 minutes. After addition, the reaction mixture was stirred, at room temperature under nitrogen for 18 hours, the volatile components removed and dissolved in 80 mL of H$_2$O and the aqueous washed with 100 mL of diethyl ether. The aqueous layer was then acidified with 1 mL of concentrated HCl (pH=1) and extracted with ether. The organic layers were combined, dried, filtered, and evaporated to give 1.75 grams of the t-butyl thioether product which was used without any further purification. To 1.75 g (5.64 mmole) of this material was added 2 mL of DMF, 4 mL of concentrated acetic acid, and 1 mL of H$_2$O. To the solution was then added 2-nitrobenzenesulfenyl chloride (1.6 g, 8.44 mmole) then stirred for 24 hours. The volatile components were removed under reduced pressure to give an oil/water mixture. To the mixture was then added 15 mL of H$_2$O, cooled to freezing, and then lyophilized overnight. After lyophilization, the remaining solid was taken up in CH$_2$Cl$_2$ and purified by flash chromatography (SiO$_2$, first with CH$_2$Cl$_2$, then with 50% diethyl ether-CH$_2$Cl$_2$ and then with 10% methanol-CH$_2$Cl$_2$) to isolate a yellow oil which crystallized upon standing to give 1.41 grams (59%) of a yellow crystalline solid: R$_f$=0.37 (SiO$_2$, 10% methanol-CH$_2$Cl$_2$). Coupling of this material to TentaGel® resin was accomplished by placing TentaGel® (3.0 g, 0.87 mmole of amine), 50 mL CH$_2$Cl$_2$ and 1 mL DIEA (6.46 mmole) in a peptide synthesis vessel and the mixture shaken for 5 minutes followed by washing with CH$_2$Cl$_2$. To this was added 20 mL CH$_2$Cl$_2$ followed by 3-[2-[(2-nitrophenyl) dithio]propionyl]-6-methoxyphenylacetic acid from above (0.9 g, 2.2 mmole) dissolved in 30 mL of CH$_2$Cl$_2$ and mixture shaken for 30 seconds. To the mixture was added (0.3 mL, 2.1 mmole) diisopropylcabodiimide (DIC) and mixture shaken for 7 hours, filtered, washed with CH$_2$Cl$_2$, methanol, and CH$_2$Cl$_2$. The resin was then placed under pump vacuum for several hours to give 3.2 grams of the final resin material as a yellow solid. The amount of disulfide on the resin was determined by a modified Ellman spectrophotometric assay at 490 nm (0.18 mmole of disulfide/g of resin). To the resin (2.3 g, 0.43 mmole) was added 150 mL DMF, β-mercaptoethanol (0.25 mL, 3.5 mmole) and diisopropylethylamine (0.4 mL, 2.3 mmole) and the mixture shaken for 2–3 minutes, filtered, and the process repeated two more times using the same quantities of BME and DIEA. The resin was then washed five times with DMF, three times with methanol, four times with CH$_2$Cl$_2$ and then three times with DMF to afford 19.

Introduction of the mono- or di-oxygen substituted bromobenzyl bromides 20, or mono- or di-oxygen substituted nitro benzylbromides 28, onto the resin to give 21 and 29: The mono- or di-oxygen substituted bromobenzyl bromides, 20 can be prepared by methods well known to those skilled in the art. For an example see the preparation of 36 and 45 below.

To resin 19 (2.3 g, 0.43 mmole) was added DMF (20 mL) followed by 20 or 28 (1.21 mmole) dissolved in 15 mL DMF. DIEA (0.5 mL, 2.87 mmole) was added and the mixture shaken for 6.5 hours, filtered, and washed five times alternatively with DMF, methanol, and CH$_2$Cl$_2$. The resin was then dried under pump vacuum to give 21 or 29.

Removal of acetate group, introduction of side chain, removal of benzoate group, and introduction of side chain to give 22 or 30: The resin bound material (46.0 g, 8.3 mmol) was placed in acetone (300 mL) and excess 2N ammonium hydroxide was added and the solution left at room temperature for 24 h (Haslam et al., J. Chem. Soc., 2137 (1964)). The resin was filtered, washed, and subjected to the following general alkylation scheme (Venuti et al., J. Med. Chem. 31, 2132 (1988)):

The required bromides are either commercially available as needed, or as the bromide having side chains which require protection with standard acid labile protecting groups. Alternatively, the alcohols are available which require conversion to the corresponding bromides or mesylates by methods known to those skilled in the art. In several cases the materials were prepared by a several step synthetic sequence as described in the specific example below.

The resin-bound material (46.0 g, 8.3 mmol) was placed in a mixture of 300 mL CHCl$_3$, 150 mL MeOH and anhydrous powdered potassium carbonate (5.0 g, 36.18 mmol) was added (18-crown-6 can be added if solubility is a problem). The reaction was heated at 50° C. for 15 min, then side chain (9.24 mmol) was added and the mixture refluxed for 4 h. After filtration, the residue was washed.

Removal of the benzoate is carried out as described by Bell (Tet. Lett., 27, 2263 (1986)). The resin-bound material (46.0 g, 8.3 mmol) was placed in toluene (300 mL) and n-butylamine (3.65 g, 50 mmol) was added. The mixture was stirred at room temperature for 3 h followed by filtration and washing of the resin.

For introduction of the second functional group, the resin-bound material (46.0 g, 8.3 mmol) was placed in a mixture of 300 mL CHCl$_3$, 150 mL MeOH and anhydrous powdered potassium carbonate (5.0 g, 36.18 mmol) was added (18-crown-6 can be added if solubility is a problem). The reaction was heated at 50° C. for 15 min, then side chain (9.24 mmol) was added and the mixture refluxed for 4 h. After filtration, the resin was washed in standard fashion to afford 22 and 30.

Preparation of diphenylsulfide 24: The resin-bound bromo group of 22 is first converted to the corresponding SH group by reaction with NaSH in DMF. Compound 22 (5 g, 1 mmol) is placed in DMF (50 mL) and NaSH (0.56 g, 10 mmol) was added. The reaction mixture was heated at 50° C. overnight, the reaction filtered, then washed alternatively with DMF and MeOH several times followed by drying the resin in vacuo. To this resin (5 g, 1 mmol) in DMF (50 mL) is added NaOH (80 mg, 2 mmol) followed by the differentially-protected dihydroxyiodobenzene 23 (3 mmol) in DMF (5 mL) and the reaction is heated with overnight to afford the desired 24 after the standard washing and drying procedures. The required iodobenzene 23 is prepared from the appropriately substituted mono or dimethoxyanilines by a series of reactions involving diazotization, iodide introduction, removal of the methoxy groups, and finally differential protection. A specific example is illustrated for the preparation of 39 below.

Reduction of nitro 30 to aniline 31: Compound 30 (5.5 g, 1.00 mmol) was placed in 10 mL DMF and to this slurry was added SnCl$_2$.2H$_2$O (2 mL of 2M solution, 4.00 mmol). The reaction vessel was shaken vigorously for 20 hr. The reaction mixture was then filtered and washed sequentially with CH$_2$Cl$_2$, CH$_3$OH, and CH$_2$Cl$_2$ to give compound 31.

Preparation of sulfonylchlorides 32: The required sulfonylchlorides are obtained commercially, or prepared either by conversion of the corresponding sulfonic acids to the desired products with phosphorous pentachloride or through direct conversion of the benzene ring to the desired product by reaction with chlorosulphonic acid. These methods are well known to those skilled in the art. A specific example is illustrated for the preparation of 49 below.

Preparation of sulfonamide 33: The resin-bound 31 (10.0 g, 2 mmol) is placed in CH$_2$Cl$_2$ (100 mL) followed by addition of the sulfonylchloride 32 (6 mmol), pyridine (2 mmol), and DMAP (0.4 mmol). The reaction is stirred at room temperature for 8 h, filtered, and washed in the usual manner to afford 33.

Removal of acetate group, introduction of side chain, removal of benzoate group, and introduction of side chain to give the fully functionalized diphenylsulfide or sulfonamide 33: The resin bound material (46.0 g, 8.3 mmol) was placed in acetone (300 mL) and excess 2N ammonium hydroxide was added and the solution left at room temperature for 24 h (Haslam et al., J. Chem. Soc., 2137 (1964)). The resin was filtered, washed, and subjected to the following general alkylation scheme (Venuti et al., J. Med. Chem. 31, 2132 (1988)):

The required bromides are either commercially available as needed, or as the bromide having side chains which require protection with standard acid labile protecting groups. Alternatively the alcohols are available which require conversion to the corresponding bromides or mesylates by methods known to those skilled in the art. In several cases the materials were prepared by a several step synthetic sequence as described in the specific example below.

The resin-bound material (46.0 g, 8.3 mmol) was placed in a mixture of 300 mL CHCl$_3$, 150 mL MeOH and anhydrous powdered potassium carbonate (5.0 g, 36.18 mmol) was added (18-crown-6 can be added if solubility is a problem). The reaction was heated at 50° C. for 15 min, then side chain (9.24 mmol) was added and the mixture refluxed for 4 h. After filtration, the residue was washed.

Removal of the benzoate is carried out as described by Bell (Tet. Lett., 27, 2263 (1986)). The resin-bound material (46.0 g, 8.3 mmol) was placed in toluene (300 mL) and n-butylamine (3.65 g, 50 mmol) was added. The mixture was stirred at room temperature for 3 h followed by filtration and washing of the resin.

For introduction of the second functional group, the resin-bound material (46.0 g, 8.3 mmol) was placed in a mixture of 300 mL CHCl$_3$, 150 mL MeOH and anhydrous powdered potassium carbonate (5.0 g, 36.18 mmol) was added (18-crown-6 can be added if solubility is a problem). The reaction was heated at 50° C. for 15 min, then side chain (9.24 mmol) was added and the mixture refluxed for 4 h. After filtration, the resin was washed in standard fashion to afford the desired products.

Deprotection and cleavage of the diphenylsulfide to afford 25, and sulfonamide 34 to afford 35: After introduction of the protected functional groups as described above, the resin-bound material (11.0 g, 2 mmol) was placed in CH$_2$Cl$_2$ (100 mL) and triflouroacetic acid (0.5 mL) added. The mixture was stirred at room temperature for one hour then the resin filtered and washed as above. The resin (3.0 g, 0.6 mmol) was suspended in 25 mL of acetonitrile. The stirred mixture was irradiated under nitrogen atmosphere using a Rayonet photochemical reactor (consisting of sixteen black light phosphor bulbs having a maximum wavelength intensity at 350 nm) for 4 hours. After irradiation, the mixture was filtered to afford the desired product 25 or 35 in solution.

Oxidation of sulfide to sulfoxide and deprotection/cleavage to afford 26: After introduction of the protected functional groups as described above, the resin-bound diphenylsulfide (11.0 g, 2 mmol) was placed in CH$_2$Cl$_2$ (100 mL) and m-chloroperbenzoic acid (2 mmol, 1 eq) was added. The reaction was allowed to stir overnight at room temperature, filtered, washed in alternating fashion with swelling (CH$_2$Cl$_2$) and shrinking (methanol) solvents, and dried in-vacuo. The resin-bound material (11.0 g, 2 mmol) was placed in CH$_2$Cl$_2$ (100 mL) and triflouroacetic acid (0.5 mL) added. The mixture was stirred at room temperature for one hour then the resin filtered and washed as above. The resin (3.0 g, 0.6 mmol) was suspended in 25 mL of acetonitrile. The stirred mixture was irradiated under nitrogen atmosphere using a Rayonet photochemical reactor (consisting of sixteen black light phosphor bulbs having a maximum wavelength intensity at 350 nm) for 4 hours. After irradiation, the mixture was filtered to afford the desired product 26 in solution.

Oxidation of sulfide to sulfone and deprotection/cleavage to afford 27: After introduction of the protected functional groups as described above, the resin-bound diphenylsulfide (11.0 g, 2 mmol) was placed in CH$_2$Cl$_2$ (100 mL) and m-chloroperbenzoic acid (4 mmol, 2 eq) was added. The reaction was allowed to stir overnight at room temperature, filtered, washed in alternating fashion with swelling (CH$_2$Cl$_2$) and shrinking (methanol) solvents, and dried in-vacuo. The resin-bound material (11.0 g, 2 mmol) was placed in CH$_2$Cl$_2$ (100 mL) and triflouroacetic acid (0.5 mL) added. The mixture was stirred at room temperature for one hour then the resin filtered and washed as above. The resin (3.0 g, 0.6 mmol) was suspended in 25 mL of acetonitrile. The stirred mixture was irradiated under nitrogen atmosphere using a Rayonet photochemical reactor (consisting of sixteen black light phosphor bulbs having a maximum wavelength intensity at 350 nm) for 4 hours. After irradiation, the mixture was filtered to afford the desired product 27 in solution.

Example 2

Experimental procedures for the preparation of: 1-Methyl-2,5'-diethoxyguanidino-3'-ethoxybenzyldiphenylsulfide 42, 1-Methyl-2,5'-diethoxyguanidino-3'-ethoxybenzyldiphenylsulfoxide 43, 1-Methyl-2,5'-diethoxyguanidino-3'-ethoxybenzyldiphenylsulfone 44, and 1-Methyl-2,5'-diethoxyguanidino-3'-ethoxybenzyldiphenylsulfonamide 52 as shown in Scheme V.

Introduction of 2-acetoxy-4-bromobenzylbromide 36 onto resin 19 to give 37: Resin 19 is prepared as described in Example 1 above. 2-Acetoxy-4-bromobenzyl bromide is prepared from 2-methyl-5-nitroaniline (Aldrich) by reactions well known to those skilled in the art of organic synthesis. The preferred synthetic sequence proceeds by diazotization under standard conditions. The diazo compound is thermolyzed in acetic acid for 1 h at 80° C. as described in Chem. Lett., 1991, 459 to afford the corresponding acetoxy compound. The bromo group is introduced via nitro reduction, diazotization, and bromide displacement all under standard conditions and finally, the desired product is obtained by benzylic bromination with N-bromosuccinimide under standard conditions. The resin 19 (10.0 g 2.0 mmol) was suspended in 150 mL of anhydrous DMF. 2-acetoxy-4-bromobenzylbromide (3.06 g, 10 mmol) and DIEA (1.75 mL, 10 mmol) were added and the reaction mixture was agitated vigorously for 7 hr at 50° C. The resin was filtered, and washed five times with DMF, three times with methanol, and six times with $CH_2Cl_2$. The resin was then dried under pump vacuum to give 37.

Introduction of 2-acetoxy-4-nitrobenzyl bromide, 45 onto the resin 19 to give 46: Resin 19 is prepared as described in Example 1. 2-Acetoxy-4-nitrobenzyl bromide, 45 is prepared from 2-amino-4-nitrotoluene (Aldrich) by diazotization under standard conditions. The diazo compound is thermolyzed in acetic acid for 1 h at 80° C. as described in Chem Lett, 1991, 459 to afford the corresponding acetoxy compound. Finally, the desired product is obtained by reaction with N-bromosuccinimide under standard conditions. The resin 19 (10.0 g 2.0 mmol) was suspended in 150 mL of anhydrous DMF. 2-acetoxy-4-nitrobenzyl bromide 45 (2.73 g, 10 mmol) and DIEA (1.75 mL, 10 mmol) were added and the reaction mixture was agitated vigorously for 7 hr at 50° C. The resin was filtered, and washed five times with DMF, three times with methanol, and six times with $CH_2Cl_2$. The resin was then dried under pump vacuum to give 46.

Removal of acetate group and introduction of side chain to give 38 and 47: The resin bound material 37 or 46 (4.6 g, 0.83 mmol) was placed in acetone (30 mL) and excess 2N ammonium hydroxide was added and the solution left at room temperature for 24 h (Haslam et al., J. Chem. Soc., 2137 (1964)). The resin was filtered, washed, and subjected to the following general alkylation scheme of Venuti et al. (J. Med. Chem. 1988, 31, 2132).

The resin-bound material (4.6 g, 0.83 mmol) was placed in a mixture of 30 mL $CHCl_3$, 15 mL MeOH and anhydrous powdered potassium carbonate (0.5 g, 3.62 mmol) was added. The reaction was heated at 50° C. for 15 min, then (2-N-PMC-guanidino)-(1-methanesulfonyl)ethanol, (0.92 mmol, see preparation below) was added and the mixture refluxed for 4 h. After filtration, the residue was washed in the standard fashion.

Preparation of (2-N-PMC-guanidino)-(1-methanesulfonyl)ethanol: Ethanolamine (10.0 g, 0.163 mol) was dissolved in $CH_2Cl_2$ (250 mL) and imidazole (24.41 g, 0.358 mol) was added. The reaction was cooled to 0° C. and TBDMSCl (27.14 g, 0.18 mol) was added. The mixture was stirred at 0° C. for two hours then room temperature for an additional two hours. Ethyl acetate (500 mL) was added and the mixture washed with 0.5M $H_2SO_4$ (400 mL), sat'd $NaHCO_3$ (400 mL) and sat'd NaCl (400 mL), dried, evaporated and the resulting material (12.0 g, 42% yield) used as is. Formamidinesulfonic acid (1.0 g, 8.05 mmol; Tet. Lett., 29, 3183, (1988)) and the above material (1.41 g, 8.05 mmol) were dissolved in dry methanol (10 mL) and stirred for 2 h at room temperature. The solvent was as removed in vacuo and the product dissolved in acetone (27 mL), water (7 mL), and NaOH (10 mL, 3.2M) added. The reaction was cooled to 0° C. and PMCCl (3.66 g, Raylo Chemicals, Alberta, Canada) was added in acetone (8 mL). After stirring for 1 h at 0° C. the reaction was diluted with ethyl acetate, washed one time each with 25 mL sat'd $NH_4Cl$, water, and sat'd NaCl, dried and evaporated. The product was purified by flash chromatography (silica, hexane/ethyl acetate 1:1) to afford 1.71 g (46%) of desired product.

The product (0.57 g, 1.23 mmol) was dissolved in THF (10 mL), cooled to 0° C. and tetrabutylammoniumfluoride (371 mg, 1.42 mmol) added. After 30 min the reaction was worked up by diluting with ethyl acetate, washing one time each with 25 mL sat'd $NH_4Cl$, water, and sat'd NaCl, dried and evaporated. The product was purified by flash chromatography (silica, $CH_2Cl_2$/methanol; 19:1) to afford 0.43 g (94%) of desired product. This material (64 mg, 0.186 mmol) was dissolved in $CH_2Cl_2$ (2 mL), cooled to 0° C. and DMAP added (2.2 mg). Methanesulfonyl chloride (35.6 mg, 0.204 mmol) was added and reaction was complete after 20 min. Evaporation of the mixture was followed by purification (silica, $CH_2Cl_2$) to afford 95 mg (92% yield) of desired product.

Preparation of substituted iodobenzene 39, conversion of 38 to the corresponding thiol, and formation of diphenylsulfide 40: 3,5-Dihydroxyiodobenzene was prepared from 3,5-dimethoxyaniline (Aldrich) by diazotization and iodine introduction followed by demethylation of the methoxy groups all under standard conditions. This material (3.78 g 16.0 mmol) was dissolved in $CH_2Cl_2$ (30 mL). Triethylamine (11.15 mL, 80 mmol), acetic anhydride (4.55 mL, 48 mmol) and DMAP (390 mg, 3.2 mmol) were added and the reaction stirred for 16 h. The reaction was evaporated to dryness, and passed through a plug of silica gel eluting with 4:1 hexane:ethyl acetate to afford the desired product. This material (12.8 mmol) was dissolved in a mix of ethanol (32 mL) and benzene (16 mL). Potassium hydroxide (0.72 g, 12.8 mmol) was dissolved in 8 mL ethanol and added over 30 min. After 30 min the reaction was diluted with ether and washed with 0.5N $H_2SO_4$, sat $NaHCO_3$, sat NaCl, dried over $Na_2SO_4$, and evaporated. The product was recrystallized from toluene to afford 86% yield of the monoacetate which was dissolved in $CH_2Cl_2$ (50 mL) and triethylamine (3.45 mL, 24.8 mmol), DMAP (0.3 g, 2.5 mmol) and benzoyl chloride (1.8 mL, 15.5 mmol) was added. The reaction was complete in 10 min then diluted with $CH_2Cl_2$ and washed with sat $NH_4Cl$, sat $NaHCO_3$, and sat NaCl. The solution was dried ($Na_2SO_4$) and evaporated. Purification was accomplished via silica chromatography 19:1 hexane:ethyl acetate to afford 4.4 g (95% yield) of desired product 39.

The bromo compound 38 is converted to the corresponding thiol by placing 38 (5.5 g, 1 mmol) in DMF (50 mL) and adding NaSH (0.56 g, 10 mmol). The reaction is heated at 50° C. overnight, filtered, and washed successively with DMF and methanol (3×). The final washing is with $CH_2Cl_2$ then the resin is dried briefly. The conversion of the resin bound thiol to the corresponding diphenyl sulfide can be accomplished by reaction of the thiol sodium salt with the iodobenzene 39 in DMF. The sodium salt of the resin bound thiol (5.5 g, 1.0 mmol) was prepared by adding sodium hydroxide (40 mg, 1.0 mmol) to the resin in DMF (50 mL). The mixture was heated at 50° C. for 1 h then 3-acetoxy-5-benzyloxyiodobenzene (1.15 g, 3 mmol) is added and the reaction stirred overnight at 50° C., cooled, then filtered and washed in standard fashion to afford resin bound diphenyl sulfide 40.

Reduction of nitro 47 to aniline 48: Compound 47 (5.5 g, 1.0 mmol) was placed in 10 mL DMF and to this slurry was added $SnCl_2.2H_2O$ (2 mL of 2M solution, 4.00 mmol). The reaction vessel was shaken vigorously for 20 hr. The reaction mixture was then filtered and washed sequentially with 20 mL $CH_2Cl_2$ (3×), 20 mL $CH_3OH$ (3×), and 20 mL $CH_2Cl_2$ (3×) to give compound 48.

Preparation of sulfonyl chloride 49: 3,5-Dihydroxysulfonic acid (19.0 g, 0.1 mol) was dissolved/suspended in $H_2O$. The pH was adjusted to 8 with 10% NaOH. Bromobenzene (300 mL) was added and NaOH (60 mL) and benzoyl chloride (18 mL) were added via dropping funnel together over 30 min. The reaction was stirred for an additional 1 hr, filtered, washed with 150 mL bromobenzene and then twice with 500 mL warm water until the filtrate was pH 7. The water washings were back extracted with ethyl acetate (2×50 mL), dried and evaporated. The combined solids were dried in vacuo and recrystallized from 90 mL ethyl acetate and 80 mL hexane to afford 13.2 g (33% unoptimized yield) of desired monobenzoate. This material (13.2 g, 33 mmol) was dissolved in $CH_2Cl_2$ (100 mL) and triethylamine (5.5 g, 70 mol) and acetic anhydride (7.15 g, 70 mmol) was added. The reaction was cooled in an ice bath and DMAP (0.25 g) added. The mixture was stirred overnight and allowed to warm to room temperature during this period. The reaction was diluted with ethyl acetate, washed with sat $NH_4Cl$, sat NaCl, back extracted with ethyl acetate, dried, and evaporated. The material remaining was purified by quick pass through silica gel. This monobenzoate-monoacetate sulfonic acid (3.54 g, 10 mmol) was dissolved in 50 mL $CH_2Cl_2$ and cooled to 0° C. under an argon atmosphere and phosphorous pentachloride (4.16 g, 20 mmol) added. After 4 hr at 50° C., the reaction was worked up and purified to afford 49.

Preparation of sulfonamide 50. The resin-bound 48 (11.0 g, 2 mmol) was suspended in $CH_2Cl_2$ (100 mL). To this was added 3-acetoxy-5-benzyloxybenzenesulfonyl chloride 49 (2.12 g, 6 mmol), pyridine (475 mg, 6 mmol), and DMAP (50 mg, 0.4 mmol). The reaction was stirred at room temperature for 8 h, filtered, and washed in the usual manner with $CH_2Cl_2$ and MeOH to afford 50.

Removal of acetate group, introduction of side chain, removal of benzoate group, and introduction of side chain to afford 41 and 51: The resin bound material (46.0 g 8.3 mmol) was placed in acetone (300 mL) and excess 2N ammonium hydroxide was added and the solution left at room temperature for 24 h (Haslam et al., J. Chem. Soc., 2137 (1964)). The resin was filtered, washed, and placed in a mixture of 300 mL $CHCl_3$, 150 mL MeOH and anhydrous powdered carbonate (5.0 g, 36.18 mmol) was added. The reaction was heated at 50° C. for 15 min, then (2-bromoethyl)benzene (1.71 g, 9.24 mmol, Aldrich) was added and the mixture refluxed for 4 h. After filtration, the residue was washed. Removal of the benzoate is carried out as described by Bell (Tet. Lett., 27, 2263 (1986)). The resin-bound material (46.0 g, 8.3 mmol) was placed in toluene (300 mL) and n-butylamine (3.65 g, 50 mmol) was added. The mixture was stirred at room temperature for 3 h followed by filtration and washing of the resin. For introduction of the second functional group, the resin-bound material (46.0 g, 8.3 mmol) was placed in a mixture of 300 mL $CHCl_3$, 150 mL MeOH and anhydrous powdered carbonate (5.0 g, 36.18 mmol) was added. The reaction was heated at 50° C. for 15 min, then (2-N-PMC-guanidino)-(1-methanesulfonyl)ethanol, 40 (9.24 mmol, see preparation above) was added and the mixture refluxed for 4 h. After filtration, the residue was washed and dried.

Deprotection of functional groups and cleavage from the resin to afford 42 and 52: The resin-bound material (11.1 g, 2 mmol) was placed in $CH_2Cl_2$ (100 mL) and trifluoroacetic acid (2.0 mL) added. The mixture was stirred at room temperature for one hour then the resin filtered and washed. The resin bound material (3.3 g, 0.6 mmol) was suspended in 50 mL of acetonitrile. The stirred mixture was irradiated under nitrogen atmosphere using a Rayonet photochemical reactor (consisting of sixteen black light phosphor bulbs having a maximum wavelength intensity at 350 nm) for 4 hours. After irradiation, the mixture was filtered to afford the desired products 42 and 52 in solution.

Oxidation of sulfide 41 to sulfoxide and deprotection/cleavage to afford 43. The resin-bound diphenylsulfide 41 (11.0 g, 2 mmol) was placed in $CH_2Cl_2$ (100 mL) and m-chloroperbenzoic acid (0.35 g, 2 mmol, 1 eq) was added. The reaction was allowed to stir overnight at room temperature, filtered, washed in alternating fashion with swelling ($CH_2Cl_2$) and shrinking (methanol) solvents, and dried in-vacuo. The resin-bound material (11.0 g, 2 mmol) was placed in $CH_2Cl_2$ (100 mL) and triflouroacetic acid (0.5 mL) added. The mixture was stirred at room temperature for one hour then the resin filtered and washed as above. The resin (3.0 g, 0.6 mmol) was suspended in 25 mL of acetonitrile. The stirred mixture was irradiated under nitrogen atmosphere using a Rayonet photochemical reactor (consisting of sixteen black light phosphor bulbs having a maximum wavelength intensity at 350 nm) for 4 hours. After irradiation, the mixture was filtered to afford the desired product 43 in solution.

Oxidation of sulfide 41 to sulfone and deprotection/cleavage to afford 44. The resin-bound diphenylsulfide 41 (11.0 g, 2 mmol) was placed in $CH_2Cl_2$ (100 mL) and m-chloroperbenzoic acid (0.7 g, 4 mmol, 2 eq) was added. The reaction was allowed to stir overnight at room temperature, filtered, washed in alternating fashion with swelling ($CH_2Cl_2$) and shrinking (methanol) solvents, and dried in-vacuo. The resin-bound material (11.0 g, 2 mmol) was placed in $CH_2Cl_2$ (100 mL) and triflouroacetic acid (0.5 mL) added. The mixture was stirred at room temperature for one hour then the resin filtered and washed as above. The resin (3.0 g, 0.6 mmol) was suspended in 25 mL of acetonitrile. The stirred mixture was irradiated under nitrogen atmosphere using a Rayonet photochemical reactor (consisting of sixteen black light phosphor bulbs having a maximum wavelength intensity at 350 nm) for 4 hours. After irradiation, the mixture was filtered to afford the desired product 44 in solution.

Example 3
Protein Kinase C Activity Determination

Compounds of the invention are tested for ability to inhibit protein kinase C using rat brain as the enzyme source accordingly to widely used procedures such as described by A. C. McArdle and P. M. Conn, Methods in Enzymology (1989) 168, 287–301, and by U. Kikkawa et al., Biochem. Biophys. Res. Commun. (1986), 135, 636–634.

Alternatively, protein kinase C activity is determined using purified human protein kinase C isozymes by methods such as described in P. Basta et al., Biochim. Biophys. Acta. (1992) 1132, 154–160.

Example 4

Membrane Receptor Affinity Determinations

A. Bradykinin Receptor

The bradykinin receptor affinity of compounds prepared according to this invention is determined by testing for ability to displace [$^3$H] bradykinin binding from guinea pig ileal membrane as described in S. G. Farmer et al., J. Pharmacol. Exp. Ther. (1989) 248, 677.

B. Other Receptors

Generally applicable methods for testing receptor affinity of the compounds of the invention are described by H. I. Yamamura et al., Methods in Neurotransmitter Receptor Analysis, Raven Press, 1990.

Example 5

Measurement of Interaction with Target Enzymes

A. Angiotensin Converting Enzyme

Methods useful for determining the ability of compounds of the invention to inhibit angiotensin converting enzyme are disclosed by J. W. Ryan, Methods in Enzymology (1988) 164, 194–211.

B. Phospholipase $A_2$

A procedure useful to test efficacy of the invented compounds in inhibiting phospholipase $A_2$ is described by J. Reynolds et al., Methods in Enzymology (1991) 197, 3–23.

Example 6

Determination of Ion Channel Binding Xenopus oocytes are well known as tools for studying ion channels and receptors. A. L. Buller and M. M. White have described methods useful to measure interaction between compounds of the invention and various ion channels or receptors. Methods in Enzymology (1992) 207, 368–375.

Example 7

Transcription Factor Effects

J. M. Gottesfeld is an example of a reference describing a procedure suitable for analyzing the ability of the invented compounds to influence transcription factor function. Methods in Enzymology (1977) 170, 346–359.

The disclosures of all references cited in this specification herein are incorporated in their entireties by reference.

What is claimed is:

1. A library having the formula:

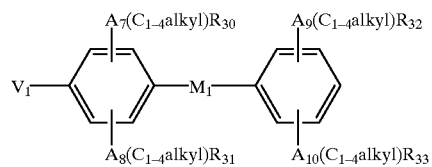

wherein:

$M_1$ is S, SO, $SO_2$, $SO_2NR'$, or $NR'SO_2$, wherein R' is H or $C_{1-6}$alkyl;

$V_1$ is H or $CH_3$;

$A_7$, $A_8$, $A_9$, and $A_{10}$ independently are absent or present as O provided that at least three are O; and $R_{30}$, $R_{31}$, $R_{32}$, and $R_{33}$ independently are OH, $NH_2$, $CO_2H$, phenyl, substituted phenyl, $CONH_2$, $NR_{80}C(NR_{81})NR_{82}R_{83}$, $C_{1-6}$alkyl, imidazole or indole wherein $R_{80}$ to $R_{83}$ independently are H or $C_{1-4}$alkyl.

* * * * *